United States Patent [19]

Yang et al.

[11] Patent Number: 5,457,230
[45] Date of Patent: Oct. 10, 1995

[54] METHOD FOR REMOVING IODINE COMPOUND FROM ACETIC ACID

[75] Inventors: O. Bong Yang; Young G. Kim; Jae C. Kim; Jae S. Lee; Hee J. Yang, all of Pohang, Rep. of Korea

[73] Assignees: Pohang Iron & Steel Co., Ltd.; Research Institute of Industrial Science & Technology, both of Kyong Sang Book-Do, Rep. of Korea

[21] Appl. No.: 341,611

[22] PCT Filed: Mar. 30, 1994

[86] PCT No.: PCT/KR94/00027

§ 371 Date: Nov. 17, 1994

§ 102(e) Date: Nov. 17, 1994

[87] PCT Pub. No.: WO94/22804

PCT Pub. Date: Oct. 13, 1994

[30] Foreign Application Priority Data

Mar. 31, 1993 [KR] Rep. of Korea .................... 1993/5318

[51] Int. Cl.$^6$ ............................ C07C 51/42; B01D 15/04
[52] U.S. Cl. ............................ 562/608; 210/690; 210/694; 210/908
[58] Field of Search ............................ 562/608; 210/690, 210/694, 908

[56] References Cited

U.S. PATENT DOCUMENTS

| | | | |
|---|---|---|---|
| 3,709,705 | 1/1973 | Hagedorn | 106/54 |
| 3,838,554 | 10/1974 | Wilhelm et al. | 55/71 |
| 3,943,229 | 3/1976 | Keener et al. | 423/240 |
| 4,029,553 | 6/1977 | Price | 203/94 |
| 4,087,623 | 5/1978 | Sherwin et al. | 560/246 |
| 4,088,737 | 5/1978 | Thomas et al. | 423/240 |
| 4,246,195 | 1/1981 | Szecsi | 260/549 |
| 4,615,806 | 10/1986 | Hilton | 210/690 |
| 4,664,753 | 5/1987 | Erpenbach et al. | 203/29 |
| 4,792,420 | 12/1988 | Rizkalla | 260/546 |

FOREIGN PATENT DOCUMENTS

| | | | |
|---|---|---|---|
| 0196173 | 10/1986 | European Pat. Off. | C07C 51/47 |
| 50-126610 | 4/1975 | Japan | C07C 53/08 |

OTHER PUBLICATIONS

"Removal of Methyl Iodide by Impregnated Charcoals from Flowing Air Under Humid Condition", Journal of Nuclear Science and Technology, vol. 9, No. 4, Apr. 1972; pp. 197–202; S. Kitani, T. Noro and T. Kohara.

*Primary Examiner*—Arthur C. Prescott
*Attorney, Agent, or Firm*—Webb Ziesenheim Bruening Logsdon Orkin & Hanson

[57] ABSTRACT

The present invention discloses a method for removing iodine compounds from acetic acid, in which the iodine compound is removed by using a solid adsorbent in the form of an activated carbon fiber having a large strength, a large bulk density, and a large specific surface, so that the treatment of large amounts should be possible, that the acetic acid should not be contaminated during the extraction of foreign materials from the adsorbent, and that the adsorbent can be repeatedly used by regenerating it. The method includes the steps of: preparing a filter in the usual manner by using an activated carbon fiber as the adsorbent; and making acetic acid containing an iodide pass through the activated carbon fiber filter, whereby the iodide in acetic acid is removed by being adsorbed by the activated carbon fiber filter.

9 Claims, 1 Drawing Sheet

METHOD FOR REMOVING IODINE COMPOUND FROM ACETIC ACID

The application is a 371 of PCT/KR94/00027 Mar. 30, 1994.

FIELD OF THE INVENTION

The present invention relates to a method for removing iodine compounds, which is applicable to the process for preparing acetic acid. Particularly, the present invention relates to a method for removing iodine compound by using activated carbon fibers as the adsorbent.

BACKGROUND OF THE INVENTION

Generally, in the case where acetic acid is prepared based on the methanol carbonylation reaction, the iodine compound is used as the reaction promoting agent in the form of methyl or hydrogen iodide ($CH_3I$ or $HI$).

The iodide which is used as the reaction promoting agent is mostly recovered by distillation.

However, usually the iodine compound remains in the form of iodine ions $I^-$, iodine molecules $I_2$, or alkyl iodine (particularly methyl iodine) in small amounts of several or several scores ppm.

In the case where acetic acid in which such small amount of iodine compound remains is used as the raw material, if the catalyst is very sensitive to the small amount of the iodine compound, the concentration of the iodine compound used as the raw material has to be lowered to an extremely small amount (several scores ppb) so as for the iodine compound to be suitable to the process.

Thus it is required that the concentration of the iodine compound remaining in the acetic acid be lowered to an extremely low level.

As the conventional iodine or iodine compound (to be called iodides) removing methods, there is an oxidation method (U.S. Pat. No. 3,709,705), methods using chemicals as a scavenger (U.S. Pat. Nos. 4,246,195 and 4,664,753), a hydrogenation method (U.S. Pat. No. 4,792,420), a distillation method (U.S. Pat. No. 4,029,553), and a crystallizing method (Japanese Patent Laid-open No. Sho-50-126610).

In these methods, although there are some differences, the cost for the distillation or the cost for the chemical salts constitutes the major expenses, thereby making them uneconomical. Further, the regeneration of the chemical salts used is difficult.

Meanwhile, there is known a method in which the iodine compound is removed by using a solid adsorbent. This method is different from the above cited methods, and has an advantage that the expense for the distillation and the expense of the chemical substance can be saved.

The typical methods are: the method using ion exchange resin (U.S. Pat. No. 3,943,229), the method using zeolite with a metal supported therein (U.S. Pat. No. 4,088,737), the method using silica with a metal supported therein (U.S. Pat. No. 3,838,554), the method using a ceramic with triethylene diamine supported therein, and the method using an activated charcoal with $SnI_2$ supported therein (J. Nucl. Science and Technol 9(4), 197, 1972). All the above methods remove the iodine compound by using the adsorbent.

However, in the case where the iodine compound is removed by using a solid adsorbent, not only the treatment of large amounts is impossible, but also the metal salts supported on the adsorbent or the chemical compounds are extracted, thereby contaminating the acetic acid.

SUMMARY OF THE INVENTION

The present inventors made studies on how to solve the problem of the conventional methods, and the present invention is based on these studies.

It is the object of the present invention to provide a method for removing iodine compounds from acetic acid, in which the iodine compound is removed by using a solid adsorbent agent in the form of an activated carbon fiber having a high strength, a large bulk density, and a large specific surface area, so that the treatment of large amounts should be possible, and the acetic acid should not be contaminated by the foreign materials extracted from the adsorbent, and the adsorbent can be repeatedly used by regenerating it.

BRIEF DESCRIPTION OF THE DRAWINGS

The above object and other advantages of the present invention will become more apparent by describing in detail the preferred embodiment of the present invention with reference to the attached drawings in which.

DESCRIPTION OF THE PREFERRED EMBODIMENT

Figure 1:
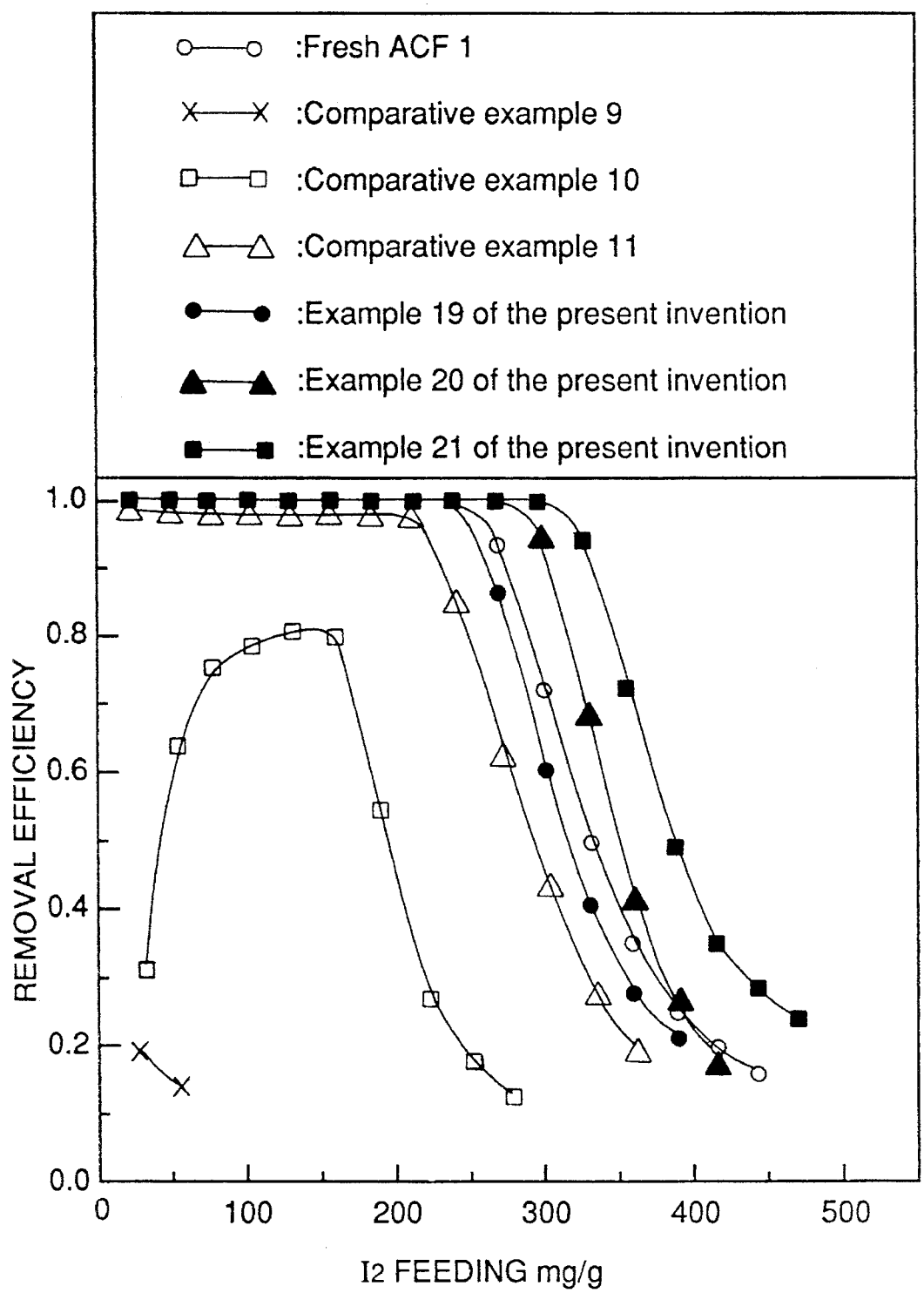
FIG. 1 is a graphical illustration of the regeneration of activated carbon fiber with $N_2$ flushing at the temperature of 20°–400° C. The iodine removal efficiency is plotted in FIG. 1 against $I_2$ feeding defined as milligram of $I_2$ fed to the adsorbent bed per gram of adsorbent accumulated from the start of the run to the point when the measurement was made.

The present invention provides a method for removing the iodine compounds from acetic acid by using a solid adsorbent. The solid adsorbent agent is an activated carbon fiber.

The present invention will be described in more detail.

The activated carbon fiber should have preferably a strength of 100–250 MPa, a bulk density of 0.01–0.2 $g/cm^3$, and a specific surface area of 1,000–2,500 $m^2/g$.

As the method for activating the carbon fiber, there is a method for steam activating the pitch-based carbon fibers, and a method of carbonizing the carbon fiber at a high temperature after activating it by means of phosphoric acid or $ZnCl_2$. The most desirable of the aforementioned two is the steam activating method conducted at a temperature of 500°–1000° C.

In the present invention, the activated carbon fiber thus prepared can be used as a adsorbent after treated by ammonia, hydrogen gas, chlorine gas, or water.

The activated carbon fiber having the above physical properties is installed in the form of a filter, and the acetic acid containing the iodine compound is passed through the fiber filter at a certain flow rate, so that the iodine compound contained in the acetic acid is removed by being caught by the activated carbon fibers.

When the acetic acid containing the iodine compounds passes through the activated carbon fibers, the flow rate of the acetic acid should be preferably 1.0–50.0 ml/min per g of adsorbent. The reason is that, if the flow rate is less than 1.0 ml/min, the productivity becomes too low, and that, if the flow rate is more than 50 ml/min, the regeneration period for the adsorbent agent becomes too short, thereby making it uneconomical, and making it impossible to operate the apparatus continuously. Further, in the case of the latter, too much iodine compound will remain in the acetic acid.

If the regenerating period for the activated carbon fiber is considered, the more preferable flow rate of the acetic acid should be 1–10 ml/min per g of adsorbent.

Further, when the iodine compound is removed from the acetic acid, the temperature should be preferably lower than 70° C., and if the temperature is higher than 70° C., the removal efficiency of the activated carbon fiber decreases.

In the present invention, water can be used as a promoter for the removal of the iodine compound from the acetic acid. If water is used as the promoter, the iodine removal rate can be improved.

If water is to be used as the promoter, water is added to the acetic acid or is saturated in the activated carbon fiber.

Further, in order to obtain the final pure acetic acid in the practical process, a plurality of water removing steps have to be carried out. The process of the present invention should be desirably applied to the step immediately preceding the last step of removing the water content.

According to the present invention, the activated carbon fibers which have been used in removing the iodine compound from the acetic acid can be repeatedly used after regenerating them. The regenerating process is carried out in such a manner that the used activated carbon fiber is heated to a temperature of 200°–500° C. for 2.0–6.0 hours while flowing inert gases such as $N_2$, He, or argon.

If the regenerating temperature is below 200° C., the regenerating efficiency is lowered, thereby making it impossible to make a complete restoration. If the regenerating temperature is over 500° C., the activated carbon fibers may be damaged, although a complete regeneration is possible. Therefore, the regenerating temperature should come within the range of 200°–500° C.

When the iodine compound is removed from the acetic acid according to the method of the present invention, the capability of the activated carbon fiber for adsorbing the iodine compound is 200–300 mg per g of the activated carbon fiber.

The application of the present invention is not limited to the above described method, but extends to the removal of the iodine compounds from an ethanol or methanol solution or other aqueous solutions.

Now the present invention will be described based on actual examples.

<EXAMPLE 1>

(Example 1 of the present invention)

One g of an ACF1 adsorbent having 1650 $m^2/g$ (pore volume: 0.8 ml/g) was used, and 200 ml of acetic acid containing 800 ppm of iodine $I_2$ was agitated at room temperature. The amount of the removed iodine was checked per unit of time, and it was found that an equilibrium point was reached after two hours of adsorption. At the equilibrium point, 305 mg of iodine was removed per g of activated carbon fiber (ACF).

The ACF1 represents the activated carbon fiber which is obtained by activating the pitch-based carbon fiber by steaming.

<Comparative Examples 1–6>

The process was carried out in the same manner as that of Example 1, except that, instead of the activated carbon fiber, the various adsorbents as shown in Table 1 below were used. The amount of iodine removed per g adsorbent and the time to reach equilibrium are as shown in Table 1 below.

TABLE 1

| Example No. | Adsorbent (1 g) | Spc srf area ($m^2/g$) | $I_2$ removed per g adsorbent (mg/g) | Eqtime (h) |
|---|---|---|---|---|
| C. Example 1 | Actvtd carbon | 860 | 195 | 24 |
| C. Example 2 | Ag/NaY[1] | 550 | 235 | 24 |
| C. Example 3 | Ag/Amb[2] | 300 | 180 | 24 |
| C. Example 4 | NaY-zeolite | 580 | 0 | — |
| C. Example 5 | $SiO_2$ | 350 | 0 | — |
| C. Example 6 | $Al_2O_3$ | 200 | 0 | — |

1. Ag/NaY indicates that in which 2 wt % Ag is ion-exchanged in NaY.
2. Ag/Amb indicates that in which 2 wt % Ag is ion-exchanged in Amberlyst XN 1010 (trade name).

According to the above results, in the case where the activated carbon fiber is used as the adsorbent, the equilibrium time is shorter than the cases of the comparative examples (1–6), and the iodine removal amount is much larger.

<EXAMPLE 2>

(Example 2 of the present invention)

One g of the ACF1 adsorbent (having a specific surface area of 1650 $m^2/g$) was filled into a glass tube having a diameter of 15 mm, so that 10 ml of uniform adsorbent should be formed. Then 1 cm layers of glass fibers were filled in the upper and lower portions of the adsorbent to support the adsorbent.

The adsorbent was maintained at the room temperature, and then, an acetic acid solution containing 800 ppm of iodine was made to pass through the adsorbent from above downward by means of a liquid pump. Under this condition, the flow rate was varied within the range of 1.0–50.0 ml/min as shown in Table 2 below.

Then 3 ml of the solution which has passed through adsorbent was taken as a test sample to measure the average concentration of iodine within the acetic acid.

The iodine concentration within the acetic acid before the filtering is indicated by $C_0$, while the average concentration of the iodine within 3 ml of the effluent acetic acid is called C. The iodine removal efficiency (%) by the adsorbent was calculated based on a formula $[(C_0-C)/C_0] \times 100$.

The point at which the iodine removal efficiency is lowered to 99.8% is called $E_1$. Then the time $T_1$ which elapsed before $E_1$ is reached in accordance with the flow rate, and the cumulative iodine removal amount $R_1$ until the time $T_1$, are as shown in Table 2 below.

TABLE 2

| Example No. | Flow rate (ml/min) | $T_1$ (min) | $R_1$ (mg/g) |
|---|---|---|---|
| Example of prsnt invtn | | | |
| 3 | 1 | 325 | 260.0 |
| 4 | 1.7 | 184 | 250.2 |
| 5 | 3.5 | 86 | 240.8 |

TABLE 2-continued

| Example No. | Flow rate (ml/min) | $T_1$ (min) | $R_1$ (mg/g) |
|---|---|---|---|
| 6 | 7 | 37.5 | 212.8 |
| 7 | 16 | 26 | 208.0 |
| 8 | 25 | 10 | 200.0 |
| 9 | 50 | 5 | 193.7 |

As shown in table 2 above, the smaller the flow rate of the acetic acid, the longer the regenerating period, i.e., the time, $T_1$, which is the time elapsed before reaching $E_1$, as well as increasing the accumulated iodine removal amount.

<EXAMPLE 3>

(Example 10–14 of the present invention)

The processes were carried out in the same manner as that of Example 2, except that the flow rate is 1.7 ml/min, and that 1 g each of ACF2, ACF3, ACF4, ACF5 and ACF6 as the adsorbent was used as shown in Table 3 below. The time $T_1$ which elapsed before arriving at $E_1$, and the cumulative iodine removal amount $R_1$ until the time $T_1$, were as shown in the table below.

TABLE 3

| Example No. | Adsorbent | Surface area ($m^2/g$) | $T_1$ (min) | $R_1$ (mg/g) |
|---|---|---|---|---|
| Prnt invention No. | | | | |
| 10 | ACF2 | 1550 | 170.6 | 232.0 |
| 11 | ACF3 | 1500 | 166.0 | 225.7 |
| 12 | ACF4 | 1780 | 198.8 | 270.3 |
| 13 | ACF5 | 1380 | 154.8 | 210.5 |
| 14 | ACF6 | 1280 | 143.5 | 195.1 |

In the above, ACF2 indicates an activated carbon fiber which was obtained by activating a pitch-based series carbon fiber with phosphoric acid, and by carbonizing at a temperature. ACF3 indicates an activated carbon fiber which was obtained by activating with $ZnCl_2$, and by carbonizing at a temperature. ACF 4 indicates an activated carbon fiber which was obtained by treating the ACF1 of Example 1 with ammonia at 800° C. ACF5 indicates an activated carbon fiber which was obtained by treating the ACF1 with hydrogen at 900° C. ACF6 indicates an activated carbon fiber which was obtained by treating the ACF1 with chlorine gases at 450° C.

<Comparative Examples 7 and 8>

The process was carried out in the same manner as that of Example 2, except that the flow rate of acetic acid was 1.7 ml/min, and that the adsorbent consisted of an activated carbon (specific surface area: 860 $m^2/g$) and Ag/NaY (specific surface area: 580 $m^2/g$) in which 2 wt % Ag was ion-exchanged in NaY. Here, in order to make the volume of the adsorbent layer become 10 ml, small glass beads were uniformly mixed.

When the flow rate was 1.7 ml/min, the time $T_1$ for arriving at $E_1$, and the cumulative iodine removal amount $R_1$ were as shown in Table 4 below.

TABLE 4

| Example No. | adsorbent | $T_1$ (min) | $R_1$ (mg/g) |
|---|---|---|---|
| C. Example 7 | Activated carbon | 15 | 20.4 |
| C. Example 8 | Ag/NaY | 5.0 | 6.8 |

From the above table, it is seen that the case of using ACF2-ACF6 as the adsorbent (Examples 10–14 of the present invention) is superior in $T_1$ and $R_1$ compared with the case of using an activated carbon and Ag/NaY (Comparative Examples 7 and 8).

<EXAMPLE 4>

(Example 15 of the present invention)

The process was carried out in the same manner as that of Example 2, except that the flow rate was 3.5 ml/min, and that the iodine concentration in the acetic acid was varied within the range of 15–1500 ppm as shown in Table 5 below. The time $T_1$ for arriving at $E_1$ and the cumulative iodine removal amount $R_1$ were as shown in Table 5 below.

TABLE 5

| Iodine concentration in acetic acid (ppm) | $T_1$ (min) | $R_1$ (mg/g) |
|---|---|---|
| 15 | 3053 | 160.3 |
| 100 | 511 | 178.9 |
| 300 | 172 | 180.6 |
| 500 | 106 | 185.5 |
| 1100 | 65 | 250.3 |
| 1500 | 49 | 257.3 |

As shown in Table 5 above, it is possible to remove iodine within the iodine concentration range of 15–1500 ppm.

<EXAMPLE 5>

(Example 16 of the present invention)

The process was carried out in the same manner as that of Example 2, except that the flow rate was 3.5 ml/min, and that the solvent used was methanol, ethanol, water or a mixture of 50 volume % of water and 50 volume % of acetic acid instead of pure acetic acid as shown in Table 6 below. The time $T_1$ for arriving at $E_1$ and the cumulative iodine removal amount $R_1$ until the time $T_1$ were as shown in Table 6 below.

TABLE 6

| Solvent | Iodine Concentration (ppm) | $T_1$ (min) | $R_1$ (mg/g) |
|---|---|---|---|
| Methanol | 500 | 554 | 959.5 |
| Ethanol | 800 | 79 | 221.2 |
| Water | 300 | 1533 | 1610 |
| Water 50% + Acetic acid 50% | 800 | 275 | 770 |

As shown in Table 6 above, the activated carbon fiber of the present invention can be applied not only to acetic acid but also methanol, ethanol, water and a mixture of water and acetic acid for removing iodine.

<EXAMPLE 6>

(Example 17 of the present invention)

The process was carried out in the same manner as that of Example 2, except that the activated carbon fiber ACF1 saturated with distilled water for one hour was used as the adsorbent, and that the flow rate was 3.5 ml/min. The time $T_1$ for arriving at $E_1$ and the cumulative iodine removal amount $R_1$ until the time $T_1$ were 118 minutes and 330.4 mg per g of adsorbent, respectively.

From the above results, it can be seen that the case of using water as the promoter for removing iodine from acetic acid was superior in $T_1$ and $R_1$ compared with the cases which is not used water as a promoter.

<EXAMPLE 7>

(Example 18 of the present invention)

The process was carried out in the same manner as that of Example 2, except that the flow rate was 3.5 ml/min, and that acetic acid containing 800 ppm of hydrogen iodide (HI) instead of iodine was used. The time $T_1$ for arriving at $E_1$ and the cumulative iodine removal amount $R_1$ until the time $T_1$ were 125 minutes and 350.0 mg per g of ACF1 respectively.

It is seen from the above results that the activated carbon fiber of the present invention is effective in removing not only iodine but also iodine compounds such as hydrogen iodide.

<EXAMPLE 8>

The activated carbon fiber (used material) which was used in Example 2 for removing iodine (used ACF1) was regenerated by heating at 20° C. for 24 hours (Comparative Example 9), at 100° C. for 20 hours (Comparative Example 10), at 150° C. for 12 hours (Comparative Example 11), at 200° C. for 6 hours (Example 19 of the present invention), at 300° C. for 4 hours (Example 20 of the present invention), and at 400° C. for 3 hours (Example 21 of the present invention), while flowing $N_2$ gas at a flow rate of 300 ml/min. The process was carried out in the same manner as that of Example 2 after regenerating the used ACF1, according to comparative example 9–11 and example 19–21, thereby removing iodine from the acetic acid. FIG. 1 illustrates the iodine removal efficiency of activated carbon fiber regenerated at a temperature of 20°–400° C.

As shown in FIG. 1, it is apparent that the Examples 19–21 of the present invention mostly restored the removal capacity of fresh ACF1.

According to the present invention as described above, an activated carbon fiber is used as the adsorbent, with the result that the iodine removal efficiency is markedly increased. Not only iodine, but also iodides such as hydrogen iodide, methyl iodide and the like can be removed. Further, not only from acetic acid, but also iodine can be removed from water, ethanol, methanol and a mixture of water and acetic acid. Further, the activated carbon fiber can be regenerated after use for repeated use.

What is claimed is:

1. A method for removing iodine from acetic acid by using a solid adsorbent, comprising the steps of:

preparing a filter in the usual manner by using an activated carbon fiber as the adsorbent; and making acetic acid containing an iodide pass through said activated carbon fiber filter, whereby said iodide in acetic acid is removed by being adsorbed by said activated carbon fiber filter.

2. The method as claimed in claim 1, wherein said activated carbon fiber has a strength of 100–250 MPa, a bulk density of 0.01–0.2 $g/cm^3$, and a specific surface area of 1,000–2,500 $M^2/g$.

3. The method as claimed in claim 1, wherein said activated carbon fiber is selected from a group consisting of: an activated carbon fiber obtained by activating the pitch-based carbon fiber with a steam, phosphoric acid or $ZnCl_2$; an activated carbon fiber chemically treated with ammonia, hydrogen gas or chlorine gas; and an activated carbon fiber treated with an water.

4. The method as claimed in claim 1, wherein, when acetic acid is made to pass through said activated carbon fiber filter, the flow rate of acetic acid is 1.0–50.0 ml/min per g of said activated carbon fiber.

5. The method as claimed in claim 1, wherein water is added to acetic acid, or said activated carbon fiber is made to be saturated with water, whereby water is used as the promoter for removing iodides.

6. The method as claimed in claim 4, wherein water is added to acetic acid, or said activated carbon fiber is made to be saturated with water, whereby water is used as the promoter for removing iodides.

7. A method for removing iodides from acetic acid by using a solid adsorbent, comprising the steps of:

preparing a filter by using an activated carbon fiber as a solid adsorbent;

making acetic acid containing an iodide pass through said activated carbon fiber filter to remove said iodide from acetic acid by making said iodide adsorbed by said activated carbon fiber;

making said iodide desorbed from said activated carbon fiber by heating it at a temperature of 200°–500° C. for 2–6 hours, while flowing an inert gas with oxygen excluded; and using said activated carbon fiber with said iodide desorbed as the adsorbent to remove said iodide from acetic acid.

8. The method as claimed in claim 7, wherein said inert gas is selected from a group consisting of $N_2$, He, and Ar gases and mixtures of them.

9. The method as claimed in claim 7, wherein said activated carbon filter has a strength of 100–250 MPa, a bulk density of 0.01–0.2 $g/cm^3$, and a specific surface area of 1,000–2,500 $m^2/g$.

* * * * *

UNITED STATES PATENT AND TRADEMARK OFFICE
CERTIFICATE OF CORRECTION

PATENT NO. : 5,457,230
DATED : October 10, 1995
INVENTOR(S) : Yang et al.

It is certified that error appears in the above-indentified patent and that said Letters Patent is hereby corrected as shown below:

Title page, section '[75] Inventors:', "O. Bong Yang" should read --O Bong Yang--.

Column 1 Line 27 after "such" insert --a--.

Column 1 Line 32 "ppb)" should read --ppm)--.

Column 2 Line 52 "as a" should read --as an--.

Column 4, Table 1, Line 16, 'C. Example 2, Adsorbent (1g)', "Ag/NaY$^1$" should read --Ag/NaY$^2$--.

Column 5 Line 19 "(Example 10-14" should read --(Examples 10-14--.

Column 7 Line 6 "is not used" should read --did not use--.

Claim 2 Line 10 Column 8 "M$^2$/g." should read --m$^2$/g.--.

Claim 3 Line 17 Column 8 "an water" should read --water--.

Signed and Sealed this

Twenty-first Day of May, 1996

Attest:

BRUCE LEHMAN

*Attesting Officer*     *Commissioner of Patents and Trademarks*